United States Patent [19]

Takami et al.

[11] 4,374,456
[45] Feb. 22, 1983

[54] PROCESS FOR PRODUCING A GAS DETECTING ELEMENT

[75] Inventors: Akio Takami; Thutomu Saito; Kazutoshi Tanaka, all of Nagoya, Japan

[73] Assignee: NGK Spark Plug Co., Ltd., Aichi, Japan

[21] Appl. No.: 294,122

[22] Filed: Aug. 19, 1981

Related U.S. Application Data

[62] Division of Ser. No. 139,626, Apr. 14, 1980, Pat. No. 4,328,477.

[30] Foreign Application Priority Data

Apr. 12, 1979 [JP] Japan .................................. 54-45186

[51] Int. Cl.³ ............................................... H01G 9/00
[52] U.S. Cl. ........................................ 29/588; 29/583
[58] Field of Search .................... 29/588, 583, 610 R; 427/87; 324/71 SN; 357/10, 25; 338/35, 22 R, 322, 328, 329, 308, 309

[56] References Cited

U.S. PATENT DOCUMENTS

| | | | |
|---|---|---|---|
| 3,054,709 | 3/1974 | Freestone et al. | 29/583 |
| 3,671,818 | 6/1974 | Chiba | 357/10 X |
| 3,795,048 | 3/1974 | Tachibana et al. | 29/610 R X |
| 3,816,906 | 6/1974 | Falkenberg | 29/583 |
| 4,053,864 | 10/1977 | Rodriguez et al. | 338/322 |
| 4,206,173 | 6/1980 | Yamaguchi et al. | 338/34 X |

FOREIGN PATENT DOCUMENTS 52-9842  1/1977  Japan ................................ 338/21

*Primary Examiner*—L. Dewayne Rutledge
*Assistant Examiner*—David Hey
*Attorney, Agent, or Firm*—Sughrue, Mion, Zinn, Macpeak & Seas

[57] ABSTRACT

A gas detecting element including a semiconductor wafer formed of a transition-metal oxide with an electrode layer bonded to both sides of the wafer and a protective layer overlaid on the surface of the electrode layer. A metal lead wire is attached to each electrode layer by means of an electrically conductive adhesive wherein the region at which the metal lead wire is bonded to the electrode layer is reinforced by an insulating adhesive that covers the region. A process for producing such a gas detecting element is also disclosed.

8 Claims, 9 Drawing Figures

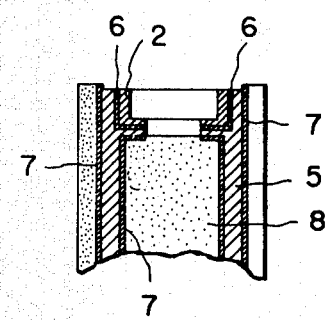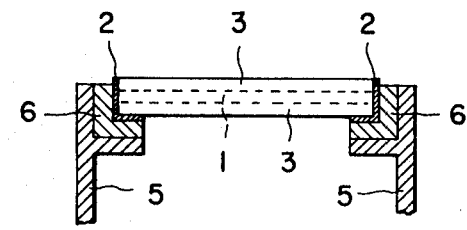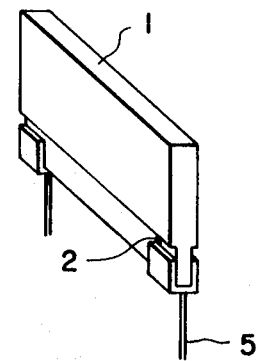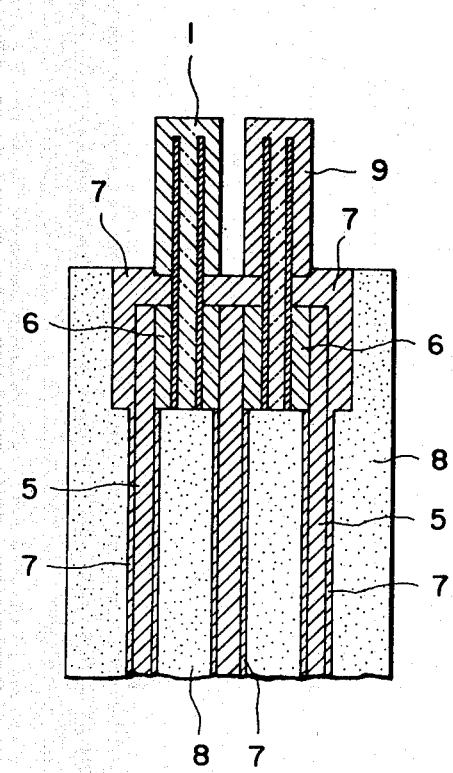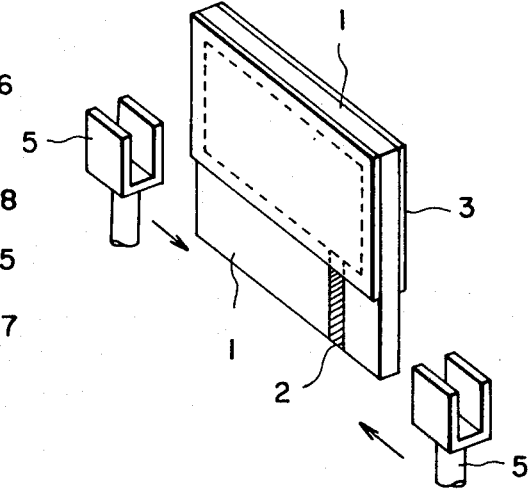

PROCESS FOR PRODUCING A GAS DETECTING ELEMENT

This is a division of application Ser. No. 139,626, filed Apr. 14, 1980, now U.S. Pat. No. 4,328,477.

BACKGROUND OF THE INVENTION

1. Field of the Invention

The present invention relates to a gas detecting element. More particularly, the invention relates to a gas detecting element specifically adapted for mass production and a process for producing such an element.

2. Description of the Prior Art

A previously known element used for detecting various gaseous components such as those in the exhaust gas generated by burning a fuel is constructed with a semiconductor wafer made of a transition-metal oxide and electrodes composed of a pair of noble metal wires one end of each of which is coupled to the wafer. To produce such detector element, a pair of noble metal bodies serving as electrodes are placed side-by-side in a mold and the mold is charged with a semiconductor material of a transition-metal oxide which is pressed into a desired element shape. With this technique, there is a difficulty in providing a product in which a space of not more than 0.1 mm between the electrodes is maintained at a high accuracy so that the electrical resistance of the element is less than 5 megohms so that a safety device inside the element can operate at low voltage. Also, the technique is unable to provide large area electrodes and thus is not advantageous for manufacturing gas detecting elements having a reduced electrical resistance.

The inventors of the present invention have previously proposed in Japanese patent application No. 40561/78 a gas detecting element constructed of a semiconductor wafer of a transition-metal oxide, platinum electrodes bonded to both sides of the wafer with electrodes connected to noble metal wires, and a porous ceramic protective layer covering the surfaces of the electrodes. When a gas detecting element of such construction is used in a normal operating temperature range for an air/fuel ratio detector for controlling the exhaust gas from an internal combustion engine, it provides an overlapping portion in the electrical resistance temperature characteristic curves even if it changes suddenly at the theoretical mixing ratio. The "overlapping portion" is defined in the commonly assigned former U.S. application Ser. No. 112,977 filed on Jan. 17, 1980. Thus, it is capable of achieving correct detection of the gases in the exhaust and thus providing information concerning the theoretical mixing ratio. However, the required method for manufacturing a detecting element of such sheet structure involves a complex step of burying metal lead wires. This has presented a serious problem that has yet to be solved before mass production of such elements can be implemented.

SUMMARY OF THE INVENTION

In accordance with the invention there is provided a gas detecting element including a semiconductor wafer composed primarily of a transition-metal oxide, an electrode layer bonded to both sides of the wafer, and a protective layer overlying the surface of the electrode layer. A metal lead wire is attached to each electrode layer by an electrically conductive adhesive and the region at which the metal lead wire is bonded to the electrode layer is reinforced by an insulating adhesive that covers that region.

As a result of various studies directed to solving the problems arising from the conventional technique, the inventors have found that the difficulty in mass production due to the complex operation required for embedding metal lead wires can be overcome by first providing a laminated sheet of wide area that yields a number of elements. Each sheet includes a semiconductor wafer composed primarily of a transition-metal oxide, electrodes of a noble metal such as platinum bonded thereto, and a porous protective layer overlying each of the electrodes with the protective layer partially cut away to provide an area for permitting a metal lead wire to be connected to each of the electrodes. The sheet is then divided into individual elements. Finally, a metal lead wire is attached to each electrode by an electrically conductive adhesive.

BRIEF DESCRIPTION OF THE DRAWINGS

FIG. 3a is a cross-sectional view of a second embodiment of a gas detecting element of the invention showing how metal lead wires are installed;

FIG. 3b is an enlarged view of a portion of FIG. 3a;

FIG. 3c is a perspective view of a third embodiment of the invention showing metal lead wire installation;

FIG. 3d is an exploded view of FIG. 3c; and

FIG. 4 is a cross-sectional view of a fourth embodiment of a gas detecting element of the invention which operates in combination with a temperature-compensated element.

DETAILED DESCRIPTION OF THE INVENTION

Figure 1A:
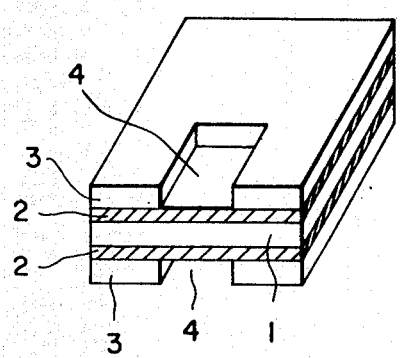
FIGS. 1a and 1b are perspective views of a first preferred embodiment of the gas detecting element of the invention before metal lead wires have been bonded thereto.

A first preferred embodiment of a gas detecting element of the invention will now be described with reference to FIG. 1 wherein reference numeral 1 indicates a semiconductor wafer composed primarily of a transition-metal oxide, 2 an electrode layer attached to both sides of the wafer, and 3 a protective layer provided to cover each electrode layer 2. The semiconductor wafer 1 is made of a fine powder of a transition-metal oxide such as titanium dioxide, vanadium oxide, iron oxide, chromium oxide, manganese oxide, nickel oxide, cobalt oxide, tin oxide or zinc oxide. In actual practice, the metal oxide is mixed with up to about 2 mol% of a sensitizing agent of a noble metal powder, for instance platinum metal power. The mixture is preferably further blended with an organic resin, such as a butyral resin, and a plasticizer to form a sheeting compound which is then shaped into a green sheet 0.1 to 2.0 mm thick using a doctor blade process.

A blank (25 mm × 25 mm) is cut out of a green tape by a punching machine. The metal electrode layer 2 provided on both sides of the blank is prepared by dispersing a butyral resin in a plasticizer to form a plastisol and mixing it with a noble metal powder such as platinum powder to form a paste. The paste is then printed on both sides of the blank using a screen process. Alternatively, the electrode layer may be prepared by a known technique of cathode sputtering, vapor deposition or other metalizing methods.

The protective layer 3 are formed on each metal electrode layer 2 by, for example, screening process, or may be composed of a tape of an insulating porous material such as titanium dioxide, aluminum oxide, or silicon oxide ceramics which is applied to the electrode layer. Alternatively, the semiconductor layer 1 may itself serve as the protective layer. FIG. 1b shows this alternative embodiment wherein the protective layer 13 has been partially cut away to expose part of the metal electrode layer 12 for permitting connection of a metal lead wire as described hereinbelow to the electrode layer by means of an electrically conductive adhesive. For ease of alignment between the lead wire and electrode layer, a groove 4 may be provided in the protective layer as shown in FIG. 1a.

Figure 1B:
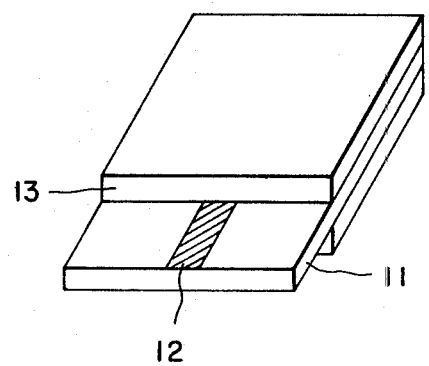
Figure 1C:
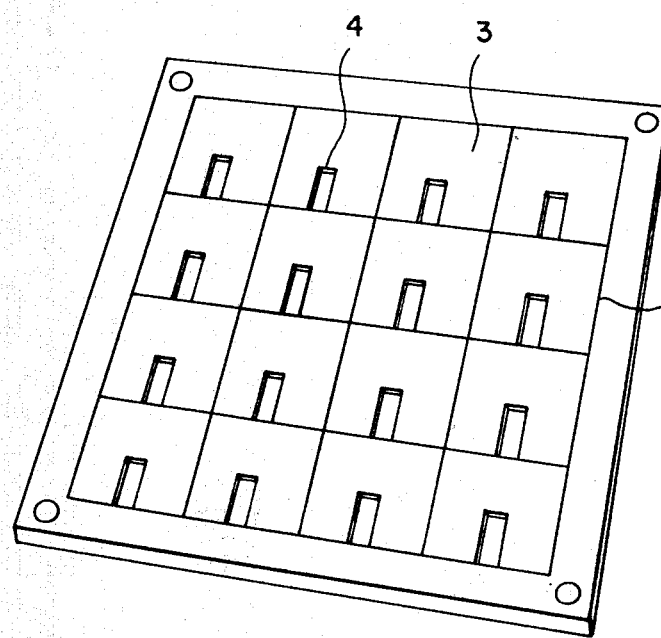
FIG. 1c shows a perspective view of a laminated structure of a blank.

A blank as described above is of a laminated structure wherein a semiconductor layer 1 composed primarily of a transition-metal oxide is sandwiched between two electrode layers 2 each of which is covered with a protective layer 3 with the area of the blank being large enough to provide a large number of detector elements as shown in FIG. 1d. The blank is then divided into individual wafer (FIG. 1a) each of which is baked, for instance, at about 1000° to 1300° C. for about 0.5 to 3 hours thereby providing a single wafer for the gas detecting elements as shown in FIG. 1 for which a metal lead wire has yet to be installed.

Figure 2:
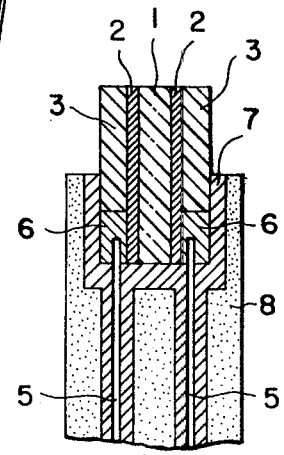
FIG. 2 is a cross-sectional view of the element shown in FIGS. 1a and 1b.

FIG. 2 is a cross-sectional view of a single wafer of gas detecting element of the invention completed by attachment of metal lead wires. In the FIG. 2, reference numeral 5 indicates a metal lead wire, for example, a heat-resistant nickel wire, or having a tip to which a noble metal wire, preferably Pt/Rh alloy wire, is welded. This wire is connected to each metal electrode 2 in the groove 4 cut in the protective layer 3 as shown in FIG. 1a. Represented by reference numeral 6 is an electrically conductive adhesive for connecting the metal lead wire 5 to the electrode layer 2. The adhesive 6 is typically made of a mixture of platinum powder and less than 10% of borosilicate glass or an electrically conductive ceramic powder such as $FeCO_2O_4$ or $La_{0.5}Sr_{0.5}CoO_3$. Reference numeral 7 designates an insulating reinforcement adhesive that covers the region where the metal lead wire 5 is secured to the electrode layer 2 through the conductive adhesive 6. Examples of such an insulating adhesive are sealants including a mixture of alumina and borosilicate glass, water glass cement, alumina cement and phosphate cement. It is to be noted that as shown in FIG. 2, the metal lead wire 5 may be disposed inside an insulating material such as an alumina insulating tube 8 provided with a slit in the top thereof. In this instance, preferably only the tip of the lead wire that contacts the conductive adhesive 6 protrudes out of the tube. The lead wire is secured to the insulator by a phosphate cement or other suitable adhesive.

A preferred method for installing the metal lead wires will now be described with reference to the drawings. First, a coating of the electrically conductive adhesive 6 is applied to that portion of the electrode layer 2 which is exposed in the groove 4 as shown in FIG. 1a. Secondly, the metal lead wire 5 is attached to the electrode layer 2 with conductive adhesive 6. The lead wire is then inserted through each of the two holes formed in the insulator tube 8. The integral unit consisting of the layers 1,2,3 and the conductive adhesive 6 together with the lead wires 5 is positioned in an open end of the insulator tube so as to permit the unit to be in alignment with the central axis of the open end. Thereafter, the insulative adhesive material 7 is filled into the open end and the holes, to thus cover the conductive adhesive 6. Following these steps, the assembly is baked at about 800° to 1100° C. to provide a final product.

In the foregoing description, the electrode layer 2 coated onto both sides of the semiconductor wafer 1 and which is composed of a transition-metal oxide is connected to metal lead wire 5 having a cylindrical tip. It is to be understood that other embodiments are possible with the gas detecting element of this invention. For instance, as shown in FIGS. 3a and 3b, an electrode layer 2 having an L-shaped cross section may be attached to the edge of each side of the semi-conductor wafer 1 and may be connected to a metal lead wire 5 with a tip having a branched shape as shown in these figures. Alternatively, as shown in FIGS. 3c and 3d, an electrode layer 2 exposed at two corners of the semiconductor wafer may be connected to a metal lead wire 5 having a generally U-shaped tip which sandwiches both the wafer 1 and the electrode layer 2. In still another embodiment, a temperature-compensated element 9 may be provided together with the gas detecting element as shown in FIG. 4.

As described hereinabove, in accordance with the basic teachings of the invention the electrode layer which covers both sides of the semiconductor wafer is connected to a metal lead wire with an electrically conductive adhesive. To manufacture a gas detecting element according to the invention, a laminated blank wafer including the semiconductor wafer and electrode layers is first prepared then is divided into individual unit wafers following which metal lead wires are installed on each unit wafer. Therefore, with the invention, the metal lead wire installation that has been a major problem in the manufacture of gas detecting elements has been considerably simplified.

The method of producing a gas detecting element according to the present invention will now be described by way of the following example which is given here for illustrative purposes only as various modifications thereof may be conceived without departing from the scope and spirit of the invention.

EXAMPLE

A mixture of titanium dioxide particles $0.3\mu$ in size and 2% of platinum particles $0.2$–$1\mu$ in size was blended with a butyral resin and a plasticizer and the blend was shaped into a green sheet 0.5 mm thick. A platinum paste composed of platinum particles $1\mu$ in size, a butyral resin and an organic solvent was printed onto both sides of the sheet by a screen process thereby forming electrode layers. A porous protective layer made of a titanium dioxide tape was bonded to both sides of the platinum-metallized green sheet with a groove cut away to make a space for connecting each electrode layer to a metal lead wire. The resulting laminate was divided into individual unit wafers which were baked at 1200° C. for one hour at atmospheric pressure. Separately from the wafers, metal lead wires each composed of a 0.6 mm diameter heat-resistant nickel alloy wire whose tip was welded to a 0.4 mm diameter Pt/13% Rh were inserted through two holes in an alumina insulator tube having a slit formed in the top thereof. The tip of the lead wire was made to protrude from the insulator tube and attached to the exposed electrode layers in the groove cut in the protective layers with the intermediary of an electrically conductive adhesive composed of 5 parts of borosilicate glass and 95 parts of platinum particles 1 to 3μ in size. The slit in the insulator where the metal lead wires were attached to the electrode layers was filled with phosphate cement and the assembly was baked at about 1100° C. to thus provide a gas detecting element having metal lead wires securely connected to electrode layers.

What is claimed is:

1. A process for producing a gas detecting element comprising the steps of: bonding electrode layers to both sides of a porous semiconductor wafer comprising primarily a transition-metal oxide, disposing a protective layer on the entire surface of said electrode layers except for regions where a metal lead wire is to be coupled to said electrode layers, dividing the wafer into individual unit wafers, heating said wafers for a predetermined time period at a predetermined temperature, coupling a metal lead wire to the surface of each said electrode layer in each said regions with an electrically conductive adhesive, and covering each said region with a reinforcing insulating material.

2. The process for producing a gas detecting element according to claim 1 wherein said predetermined temperature is in a range of 800° to 1100° C.

3. The process for producing a gas detecting element according to claim 1, wherein said step of disposing a protective layer comprises the steps of disposing a protective layer to cover each electrode layer and, forming grooves in the protective layer at a position where said metal lead wire is to be coupled to said electrode layers.

4. The process for producing a gas detecting element according to claim 1, wherein said step of disposing a protective layer comprises applying a protective layer using a screening technique to cover the electrode layer except for those regions where metal lead wire is to be coupled to said electrode layers.

5. The process for producing a gas detecting element according to claim 1, wherein said transition-metal oxide is selected from the group consisting of titanium dioxide, vanadium oxide, iron oxide, chromium oxide, manganese oxide, nickel oxide, cobalt oxide, tin oxide and zinc oxide.

6. The process for producing a gas detecting element according to claim 1, wherein said transition-metal oxide is mixed with a sensitizing agent of a noble metal powder and further blended with an organic resin.

7. The process for producing a gas detecting element according to claim 1, wherein said protective layer is an insulating porous material selected from the group consisting of ceramics of titanium dioxide, aluminum oxide and silicon oxide.

8. The process for producing a gas detecting element according to claim 1, wherein said metal lead wire comprises a heat-resistant nickel wire with a welded tip made from a noble metal wire.

* * * * *